United States Patent [19]

Juen

[11] Patent Number: 4,604,478

[45] Date of Patent: Aug. 5, 1986

[54] METHOD FOR SILALACTONE PREPARATION AND USE

[75] Inventor: Donnie R. Juen, Sanford, Mich.

[73] Assignee: Dow Corning Corporation, Midland, Mich.

[21] Appl. No.: 734,999

[22] Filed: May 17, 1985

[51] Int. Cl.$^4$ .............................. C07F 7/08; C07F 7/18
[52] U.S. Cl. .................................... 556/439; 556/438; 556/442
[58] Field of Search .................... 556/442, 439, 438

[56] References Cited

U.S. PATENT DOCUMENTS

| | | | |
|---|---|---|---|
| 2,589,446 | 3/1952 | Sommer | 260/448.2 |
| 2,635,109 | 4/1953 | Sommer | 260/448.2 |
| 2,963,500 | 12/1960 | Sommer | 260/448.2 |
| 3,395,677 | 7/1968 | Saam | 260/448.2 |
| 4,329,483 | 5/1982 | Speier | 556/436 |

*Primary Examiner*—Paul F. Shaver

*Attorney, Agent, or Firm*—George A. Grindahl

[57] ABSTRACT

Carboxyalkyl-substituted organopolysiloxanes are prepared by hydrolysis of a silalactone composition having the formula

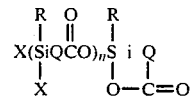

where n has an average value greater than zero, R and Q are hydrocarbon and X is Cl or Br. Silicon-containing compounds having the formula $R_a Z_b SiO_{(4-a-b)/2}$, where Z is a hydrolyzable radical, can be cohydrolyzed therewith. The silalactone composition is prepared by gently heating a mixture of an ester having the formula $X_2R\ SiQCO_2R'$ and a catalyst, such as N,N-dimethylbenzylamine.

14 Claims, No Drawings

METHOD FOR SILALACTONE PREPARATION AND USE

BACKGROUND OF THE INVENTION

The present invention relates to a method for preparing silalactones and to methods for preparing carboxyalkyl-substituted organopolysiloxanes therefrom.

Carboxyalkyl-substituted organopolysiloxanes are known from U.S. Pat. Nos. 2,723,987; 2,900,363; 3,119,855 and 3,391,177 and their utility as metal protectants and paper sizings is known from U.S. Pat. Nos. 3,755,071 and 4,011,362.

The methods disclosed in the art for the preparation of carboxyalkyl-substituted organopolysiloxanes typically comprise a hydrolysis reaction of either a cyanoalkyl-substituted hydrolyzable silane or a carbalkoxyalkyl-substituted hydrolyzable silane to prepare the carboxyalkyl-substituted siloxane unit, followed by a silanol condensation reaction and/or a siloxane equilibration reaction to provide the desired carboxyalkyl-substituted siloxane.

However, these methods for preparing carboxyalkyl-substituted organopolysiloxanes are not completely satisfactory in-as-much as the hydrolysis reaction of said cyano- or carbalkoxy-alkyl substituent is rarely complete and the final organopolysiloxane contains various amounts of residual radicals, such as cyanoalkyl radicals or carbalkoxyalkyl radicals. A method for preparing carboxyalkyl-substituted organopolysiloxanes which are free of such residual radicals is desired.

Silalactones are known from U.S. Pat. Nos. 2,589,456; 2,635,109; 2,963,500 and 3,395,167; however, the silalactones disclosed therein contain, or give rise to, triorganosiloxy units and are therefore not useful for preparing organopolysiloxanes which contain more than two carboxyalkyl substituents per molecule. Although the above-noted silalactone patents disclose that the triorganosiloxy-containing silalactones described therein are useful for preparing disiloxane dicarboxylic acids and various organo-functional organosiloxanes, no further teachings relative to carboxyalkyl-substituted organopolysiloxanes are given. Examples of said triorganosiloxy-containing or -forming silalactones of the art include

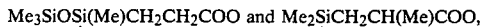

Me₃SiOSi(Me)CH₂CH₂COO and Me₂SiCH₂CH(Me)COO, wherein Me denotes the methyl radical.

U.S. Pat. No. 3,395,167 further discloses a process for preparing the triorganosiloxy-containing silalactone. Said process comprises heating an ester having the formula $XR_2Si(CR_2')_nCOOA$. The use of a catalyst to aid the reaction or the use of an ester containing two silicon-bonded X atoms was not contemplated in said patent.

Copending U.S. Ser. No. 565,075, filed on Dec. 23, 1983 and assigned to the assignee of this invention, discloses the preparation of silalactones by a process which comprises gently heating an ester in the presence of a halide salt catalyst selected from quaternary ammonium, phosphonium and pyridinium halide salts. It has now been discovered that certain tertiary amines or tertiary phosphines are effective catalysts for this process.

BRIEF SUMMARY OF THE INVENTION

It is an object of this invention to provide a method for preparing silalactone compositions. It is also an object of this invention to provide a method for preparing carboxyalkyl-substituted organopolysiloxanes which are substantially free of undesired silicon-bonded radicals. It is yet another object of the present invention to provide a one-pot method for preparing carboxyalkyl-substituted organopolysiloxanes from carbalkoxyalkyl-substituted organodihalosilanes.

These objects, and others which will become apparent upon consideration of the following disclosure and claims, are obtained by this invention which, briefly stated, comprises gently heating a compound of the formula $RX_2SiQCO_2R'$ in the presence of a tertiary amine or tertiary phosphine catalyst to provide a silalactone composition having the average formula

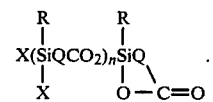

The silalactone can then be hydrolyzed, optionally, in the presence of other silicon-containing materials to provide an organopolysiloxane containing one or more siloxane units having the formula

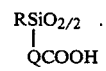

In accordance with one of the objects of this invention, carboxyalkyl-substituted organopolysiloxanes free of undesired radicals are produced by the process of this invention because the silalactone composition readily hydrolyzes and enters the siloxane structure as a carboxyalkyl-substituted silicon atom.

DETAILED DESCRIPTION OF THE INVENTION

The present invention relates to a method comprising heating, under substantially anhydrous conditions, a reaction mixture comprising a catalyst selected from the group consisting of tertiary amines and tertiary phosphines and an ester having the formula $X_2RSiQCOOR'$ wherein X denotes a chlorine or bromine atom, R denotes a monovalent hydrocarbon radical, Q denotes a divalent hydrocarbon radical, there being at least two carbon atoms in Q separating a silicon atom and a carbonyl carbon atom, and R' denotes an alkyl radical, said heating being sufficient to produce a silalactone composition having the formula

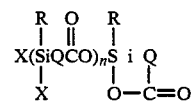

wherein X, R and Q have the meanings recited above and n has an average value greater than zero.

The present invention further relates to a method comprising mixing the silalactone composition produced by the method of this invention with water in sufficient amount to hydrolyze substantially all hydrolyzable bonds attached to silicon in the silalactone composition and to provide an organopolysiloxane containing one or more siloxane units having the formula

wherein R and Q have the stated meanings.

The silalactone compositions produced by the method of this invention have the formula

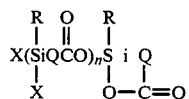

wherein n has an average value greater than zero, such as 0.5, 1.0, 3.0, 4.5, 7.7, 10 and more. It is to be noted that the silalactone compositions comprise a mixture of silalactones wherein n has a value of 0, 1, 2, 3, 4, 5, 6, 7, 8, 9, 10 or more for any particular member, the exact members of the mixture being dependent on many factors such as the nature of Q, R, X, etc. Thus, although the silalactone compositions contain monomeric silalactones (n=0), which can be separated therefrom, they are, on average, polymeric silalactones (n>0).

The silalactone compositions contain about one silicon-bonded X atom per silicon atom, where X denotes a chlorine or bromine atom. It is thought that silalactone compositions of the above formula wherein X denotes a fluorine atom or an iodine atom, although having utility for the preparing of carboxyalkyl-substituted organopolysiloxanes, are not as cleanly produced by the method of this invention as are the silalactone compositions where X is a chlorine atom or a bromine atom. That is to say, when X is a chlorine atom or a bromine atom the silalactone compositions are produced substantially freer of other products by the method of this invention than when X is fluorine or iodine. Preferably X denotes a chlorine atom.

The silalactone compositions contain about one silicon-bonded R radical per silicon atom, said R radical being a monovalent hydrocarbon radical. Examples of suitable R radicals include alkyl radicals, such as methyl, ethyl, propyl, isopropyl, n-butyl, s-butyl, t-butyl, hexyl and decyl; alkenyl radicals, such as vinyl and allyl; cycloaliphatic radicals, such as cyclohexyl; and aryl radicals, such as phenyl, benzyl and tolyl. Preferably R contains from 1 to 6 carbon atoms. Most preferably R is the methyl radical.

The silalactone compositions contain one silicon-bonded Q radical per silicon atom, wherein Q denotes a divalent hydrocarbon radical linking a silicon atom and a carbonyl carbon atom. There must be at least two carbon atoms in Q which separate the silicon atom from the carbonyl carbon atom, thereby permitting the formation of a silalactone. Examples of suitable Q radicals include alkylene radicals such as —CH₂CH₂—,

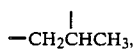

—CH₂CH₂CH₂—, —CH₂CH(CH₃)CH₂—, —(CH₂)₅—, —(CH₂)₆—, and —(CH₂)₈— and arylene radicals such as —CH₂CH₂C₆H₄CH₂—. Preferably Q contains from 2 to 5 carbon atoms. In view of the typical method for synthesizing the ester precursor to be used in the method of this invention, detailed below, Q preferably has a —CH₂ portion thereof bonded to the silicon atom.

A highly preferred silalactone composition for the method of this invention has the formula

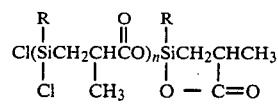

where R has the general and preferred meaning denoted above, most preferably —CH₃.

Other examples of preferred silalactone compositions for the method of this invention include the following where Ph denotes phenyl.

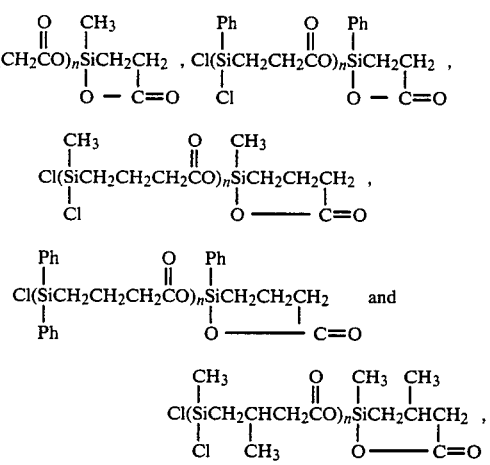

The silalactone compositions of this invention are, at the present time, most accurately characterized by spectroscopic means as illustrated by the examples disclosed below. However, they are also further characterized by chemical reactions, such as by hydrolysis to carboxyalkyl-substituted siloxane units having the formula

In the method of this invention for preparing a silalactone an ester having the formula X₂RSiQCO₂R' is gently heated in the presence of a catalyst and in the absence of liquid or gaseous water, whereupon a silalactone composition noted above and an alkyl halide having the formula R'X are coproduced.

In the above formula for the ester X, R and Q have the general and preferred meanings delineated above for the silalactone compositions and R' denotes an alkyl radical, preferably a lower alkyl radical having from 1 to 6 carbon atoms, and most preferably the methyl radical.

Examples of esters which provide preferred silalactone compositions when used in the method of this invention include the following:
Cl₂CH₃SiCH₂CHCH₃CO₂CH₃,
Cl₂CH₃SiCH₂CHCH₃CO₂CH₂CH₃,
Cl₂CH₃SiCH₂CH₂CO₂CH₃, Cl₂CH₃SiCH₂CH₂CO₂CH₂CH₃, Cl₂CH₃SiCH₂CHCH₃CH₂CO₂CH₃,
Cl₂CH₃SiCH₂CHCH₃CH₂CO₂CH₂CH₃,
Cl₂CH₃Si(CH₂)₃CO₂CH₃, Cl₂CH₃Si(CH₂)₃CO₂CH₂CH₃, Cl₂PhSiCH₂CHCH₃CO₂CH₃, $Cl_2PhSi(CH_2)_3CO_2CH_3$, $Cl_2PhSi(CH_2)_2CO_2CH_3$ and $Cl_2PhSiCH_2CHCH_3CH_2CO_2CH_3$.

Esters having the formula $X_2RSiCH_2CHQ'CO_2R'$ are typically prepared by a hyrosilylation reaction between a silane having the formula $X_2RSiH$ and an ester having the formula $CH_2=CQ'CO_2R'$ wherein Q' denotes the residue obtained when the unit $-CH_2-CH$ is removed from Q. For example, when Q denotes $-CH_2CH_2-$, Q' denotes H and when Q denotes

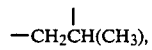

Q' denotes $CH_3$. The disclosure of U.S. Pat. No. 2,823,218 is incorporated herein by reference to teach a preferred hydrosilylation reaction and its use to prepare esters, including preferred esters that are used in the method of this invention.

By gently heated it is meant herein that the mixture of ester and catalyst is heated sufficiently, with respect to temperature and duration of heating, to prepare the silalactone composition but not so vigorously as to produce more than trace amounts of other products such as organosiloxanes, carboxylic anhydrides and acyl chlorides.

Typically the mixture of ester and catalyst is heated for 0.5 to 15 hours at a temperature of from 50° to 160° C., preferably 110° C. to 140° C. Reaction temperatures substantially higher than 160° C. produce undesirable products in that non-silalactone products are formed. In the absence of any benefit for doing otherwise one should not heat the mixture of ester and catalyst for more than 15 hours at 160° C.

The catalyst that is used in the method of this invention is selected from the group consisting of tertiary amines and tertiary phosphines.

Examples of suitable tertiary amine catalysts include, but are not limited to, alkyl amines such as $Me_3N$, $Et_3N$, $Pr_3N$, $Bu_3N$, $Me_2EtN$, $MeEt_2N$ and $BuMe_2N$; arylalkyl amines such as $Me_2BzN$ and $Et_2BzN$; cycloaliphatic amines such as $C_6H_{11}Me_2N$; and certain aromatic amines such as pyridine, quinoline and N,N-diethyl aniline. Amines having a base disassociation constant ($K_b$) of greater than $1.0 \times 10^{-9}$, and preferably greater than $1.0 \times 10^{-5}$, are preferred for the method of this invention.

Examples of suitable tertiary phosphines include, but are not limited to alkyl phosphines such as $Et_3P$ and $Bu_3P$; arylalkyl phosphines such as $Bz_3P$; and aryl phosphines, such as $Ph_3P$.

Herein Me, Et, Pr, Bu, Ph and Bz denote the methyl, ethyl, propyl, butyl, phenyl and benzyl radical, respectively.

The amount of catalyst to be mixed with the ester in the method of this invention is not critical as long as there is a sufficient amount to allow the preparation of the silalactone composition with gentle heating. Typically from 0.1 to 10, preferably 1 to 5, percent by weight, based on the weight of ester plus catalyst, of catalyst is used.

Although not being required a liquid diluent for the mixture of ester and catalyst can be used, if desired. Preferably said diluent is an inert liquid such as toluene or xylene.

In the method of this invention the mixture of ester and catalyst can be heated at any pressure, such as at subatmospheric, atmospheric or superatmospheric pressure and in either an open or a closed system. Preferably said heating is done in such a manner than any reaction product, such as R'X, that is co-produced with the silalactone composition and which is volatile at the heating temperature is removed from the reaction zone as it is formed. In the preferred embodiment of this invention, R'X denotes $CH_3Cl$ which readily, and substantially quantitatively, exits the reaction zone when the method is performed at atmospheric pressure in an open system; leaving the silalactone composition in the reaction zone.

The silalactone compositions that are prepared by the method of this invention are useful as precursor materials for the preparation of carboxyalkyl-substituted siloxane polymers and copolymers.

Thus, the present invention further relates to a method for preparing an organopolysiloxane which contains one or more siloxane units having the formula

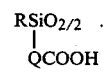

Said method comprises, in its broadest aspect, mixing a composition comprising a silalactone composition produced by the method of this invention and having the formula

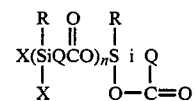

with water in sufficient amount to convert substantially all of the silalactone compositions to

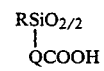

siloxane units.

The silalactone composition that is mixed with water in the method of this invention can be the general or preferred silalactone compositions that are produced by the method of this invention, hereinabove delineated. In particular the silalactone compositions that have been produced by the method of this invention can be directly converted to an organopolysiloxane without further purification.

When the silalactone composition contains no added silicon-containing components the mixing of a sufficient amount of water therewith according to the method of this invention provides a homopolymeric organopolysiloxane having the formula

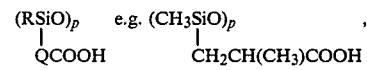

which represents cyclic and/or silanol-terminated linear organopolysiloxanes wherein p has an average value of 2 or more.

The silalactone composition to be hydrolyzed can also be mixed with a silicon-containing component having the formula $$\underset{|}{R_aSiO_{(4-a-b)/2}}$$
$$Z_b$$

in which case linear and/or cyclic copolymeric organopolysiloxanes containing one or more $$\underset{|}{RSiO_{2/2}}$$
$$QCOOH$$

siloxane units and one or more $R_aSiO_{(4-a)/2}$ siloxane units are obtained by the method of this invention. The linear copolymeric organopolysiloxanes can be silanol-terminated or organo-terminated, depending on the value of a.

Alternatively, the silicon-containing component having the formula $$\underset{|}{R_aSiO_{(4-a-b)/2}}$$
$$Z_b$$

can be added to the hydrolyzed silalactone composition and, if needed, additional water added thereto to hydrolyze any Z radicals that are present. A linear and/or cyclic copolymeric organopolysiloxane is likewise obtained therefrom.

The homopolymeric or copolymeric organopolysiloxane can, optionally, be further condensed and/or equilibrated, preferably under acid catalysis, to provide improved organopolysiloxanes with respect to the ratio of linear/cyclic siloxanes in the well-known manner. Residual acid catalyst is thereafter preferably neutralized by well-known methods.

In the above formula for the silicon-containing component R has the general and preferred meanings noted above for the silalactone compositions and Z denotes a hydrolyzable radical. Examples of suitable Z radicals include halogen atoms, such as chlorine and bromine; alkoxy radicals, such as methoxy, ethoxy and propoxy; amino and substituted amino radicals such as $-NH_2$, $-NHR$ and $-NHSiR_3$; and acyloxy radicals, such as acetoxy.

Examples of silicon-containing compounds having the formula $$\underset{|}{R_aSiO_{(4-a-b)/2}}$$
$$Z_b$$

include halosilanes, such as $R_3SiCl$, such as $(CH_3)_3SiCl$, $(CH_3)_2(CH_2=CH)SiCl$ and $(Ph)(CH_3)(CH_2=CH)SiCl$; $R_2SiCl_2$, such as $(CH_3)_2SiCl_2$, $(Ph)(CH_3)SiCl_2$ and $(CH_3)(CH_2=CH)SiCl_2$; $RSiCl_3$, such as $CH_3SiCl_3$, $(CH_2=CH)SiCl_3$ and $PhSiCl_3$; and $SiCl_4$: disiloxanes, such as $(R_3Si)_2O$, such as $(CH_3)_3SiOSi(CH_3)_3$ and $(Ph)(CH_3)(CH_2=CH)SiOSi(CH_2=CH)(CH_3)(Ph)$ and polysiloxanes, such as $(R_2SiO)_q$, such as $((CH_3)_2SiO)_q$ and $((CH_3)(CH_2=CH)SiO)_q$ where q is 3, 4, 5, 6 and more; and $R_3SiO(R_2SiO)_xSiR_3$, such as $(CH_3)_3SiO((CH_3)_2SiO)_xSi(CH_3)_3$ where x has a value of 1 or more. The values of a and b range from 0 to 3 and 0 to 4, respectively, with the total of a+b having a value of from 1 to 4.

The water that is used in the method of this invention can optionally contain one or more additives, such as acids, buffers, solvents and surfactants.

In the methods of this invention the mixing of the water and the silalactone composition can be conducted at any suitable temperature. For example, the mixing can be conducted at autogenous temperatures or heat can be added to or removed from the reaction mixture, as desired. Subsequent condensation and/or equilibration of the hydrolyzed composition is preferably conducted at elevated temperature, such as 50° to 150° C., preferably at 80° to 130° C., in the well-known manner. Neutralization of any residual acid catalyst is preferably conducted at lower temperatures, such as at room temperature.

The present invention is particularly useful for preparing organo-terminated organopolysiloxanes having the formula $$\underset{|}{R_3SiO(R_2SiO)_x(RSiO)_ySiR_3}$$
$$QCOOH$$

wherein R and Q have the meanings noted above, including the preferred embodiments thereof. The value of x can be 0 or more and the value of y can be 1 or more.

For example, a silalactone composition produced by the method of this invention can be mixed with a disiloxane having the formula $R_3SiOSiR_3$ and the mixture hydrolyzed and equilibrated under acid conditions to provide an organopolysiloxane having the formula $$\underset{|}{R_3SiO(RSiO)_ySiR_3.}$$
$$QCOOH$$

Alternatively, $R_3SiCl$ can be used with, or in place of, the $R_3SiOSiR_3$.

For another example, a silalactone composition produced by the method of this invention can be mixed with water to provide a mixture of cyclic and silanol-terminated linear organopolysiloxane having the formula $$\underset{|}{(RSiO)_y}$$
$$QCOOH$$

which can be mixed with $R_3SiO(R_2SiO)_xSiR_3$ and the mixture equilibrated to provide an organopolysiloxane having the formula $$\underset{|}{R_3SiO(R_2SiO)_x(RSiO)_ySiR_3}$$
$$QCOOH$$

wherein the values of x and y are greater than 1. Alternatively, a mixture of $R_3SiCl$ and $R_2SiCl_2$ can be used in place of $R_3SiO(R_2SiO)_xSiR_3$.

In like manner, any of the carboxyalkyl-substituted organopolysiloxanes of the art having the formula $$\underset{|}{R_3SiO(R_2SiO)_x(RSiO)_ySiR_3}$$
$$QCOOH$$

can be prepared by the method of this invention.

The carboxyalkyl-substituted organopolysiloxanes produced by the method of this invention have all of the uses disclosed in the art therefor.

The following examples are disclosed to further teach how to practice, but not to limit, the present invention which is properly delineated by the appended claims. All parts and percentages are by weight unless otherwise stated. Herein, Me denotes the methyl radical.

EXAMPLE 1

This example illustrates the preparation of a silalactone composition by the method of this invention.

A mixture of 66.4 parts of $MeCl_2SiCH_2CH(Me)CO_2Me$ and 1.3 parts of dimethylbenzylamine was heated under anhydrous conditions for 9 hours at 140° to 160° C. Methyl chloride was evolved. A viscous liquid containing some unreacted ester and a silalactone having the nominal formula $$Cl(CH_3ClSiCH_2CHCH_3CO_2)_nCH_3SiCH_2CHCH_3$$
$$\phantom{Cl(CH_3ClSiCH_2CHCH_3CO_2)_n} | \phantom{CH_3SiCH_2CH} |$$
$$\phantom{Cl(CH_3ClSiCH_2CHCH_3CO_2)_n} O \phantom{CH_3SiC} C{=}O$$

remained in the reaction vessel.

The viscous liquid was analyzed with $^1H$ nuclear magnetic resonance (n.m.r.) spectroscopy. $^1H$ n.m.r.: $Cl_2Si(C\underline{H}_3)CH_2$—, 0.82 ppm; $OClSi(C\underline{H}_3)CH_2$—, 0.65 ppm;

$$C\underline{H}_3SiCH_2CHCH_3, 0.54 \text{ ppm}; ClSi{-}O{-}SiCl, 0.36 \text{ ppm};$$
$$\phantom{CH_3SiCH_2} | \phantom{CHCH_3,} \phantom{0.54 \text{ ppm}; ClSi} | \phantom{-O-} |$$
$$\phantom{CH_3SiCH_2} O \phantom{CH} C{=}O \phantom{0.54 \text{ ppm};} C\underline{H}_3 \phantom{-O-} C\underline{H}_3$$

$$\begin{array}{c} CH_3 \\ | \\ {-}CH_2C\underline{H}C{-},2.7 \text{ ppm.} \\ \| \\ O \end{array}$$

EXAMPLE 2

When the silalactone composition produced in Example 1 is mixed with water and ether and is stirred at room temperature for 4 hours, and the resulting hydrolyzed silalactone is dried and devolatilized a waxy material is obtained which has the unit formula $$\begin{array}{c} (CH_3SiO) \\ | \\ CH_2CHCOOH \\ | \\ CH_3 \end{array}$$

EXAMPLE 3

Example 1 is repeated and 39.48 parts of the resulting silalactone composition is mixed with 4.53 parts of $H_2O$, 153.08 parts of cyclopolydimethylsiloxane and 7.44 parts of $Me_3SiO(Me_2SiO)_2SiMe_3$ and the mixture is stirred at 80° C. for about 1 hour. An equilibration catalyst (0.2 part of $CF_3SO_3H$) is added to the heated mixture and the mixture is allowed to equilibrate until the viscosity becomes constant (4 hours). The fluid is cooled, the catalyst and residual HCl is neutralized with $NaHCO_3$, dried and filtered and provides a fluid having the formula $$\begin{array}{c} Me_3SiO(Me_2SiO)_{88}(MeSiO)_{10}SiMe_3 \\ | \\ CH_2CHCOOH \\ | \\ CH_3 \end{array}$$

and a viscosity of 1800 centistokes (0.0018 $m^2/s$) at 25° C.

That which is claimed is:

1. A method comprising heating, under substantially anhydrous conditions, a reaction mixture comprising a catalyst selected from the group consisting of tertiary amines and tertiary phosphines and an ester having the formula $X_2RSiQCOOR'$ wherein X denotes a chlorine or bromine atom, R denotes a monovalent hydrocarbon radical, Q denotes a divalent hydrocarbon radical, there being at least two carbon atoms in Q separating a silicon atom and a carbonyl carbon atom, and R' denotes an alkyl radical, said heating being sufficient to produce a silalactone composition having the formula $$\begin{array}{ccc} R & O & R \\ | & \| & | \\ X(SiQCO)_n S & i & Q \\ | & & | \quad | \\ X & & O{-}C{=}O \end{array}$$

wherein X, R and Q have the meanings recited above and n has an average value greater than zero.

2. A method according to claim 1 wherein said heating is accomplished at a temperature of from about 50° to about 160° C. and the catalyst is a tertiary amine having a $K_b$ greater than $1.0 \times 10^{-5}$.

3. A method according to claim 2 wherein any reaction products that are co-produced with the silalactone composition, and which are volatile during said heating, are removed from the reaction mixture as they are formed.

4. A method according to claim 3 wherein X denotes a chlorine atom.

5. A method according to claim 4 wherein Q contains from 2 to 5 carbon atoms and R and R' each contains from 1 to 6 carbon atoms.

6. A method according to claim 5 wherein Q denotes $$\begin{array}{c} | \\ {-}CH_2CHCH_3, \end{array}$$

the —$CH_2$ portion thereof being bonded to a silicon atom.

7. A method according to claim 6 wherein R denotes —$CH_3$.

8. A method according to claim 1 further comprising mixing water with the silalactone composition in sufficient amount to hydrolyze substantially all hydrolyzable bonds attached to silicon in the silalactone composition and to provide an organopolysiloxane containing one or more siloxane units having the formula $$\begin{array}{c} RSiO_{2/2} \\ | \\ QCOOH \end{array}$$

wherein R and Q have the stated meanings.

9. A method according to claim 8 wherein X denotes a chlorine atom.

10. A method according to claim 9 further comprising mixing with the silalactone composition or the hydrolyzed silalactone composition a silicon-containing compound have the unit formula $$R_aSiO_{(4-a-b)/2}$$
$$|$$
$$Z_b$$

wherein R is as recited above, Z denotes a hydrolyzable radical, a has an average value of from 0 to 3, b has an average value of from 0 to 4 and a+b has an average value of from 1 to 4 to provide an organopolysiloxane containing one or more siloxane units having the formula $$RSiO_{2/2}$$
$$|$$
$$QCOOH$$

and one or more siloxane units having the formula $R_aSiO_{(4-a)/2}$ wherein a, R and Q have the stated meanings.

11. A method according to claim 10 wherein the organopolysiloxane has the formula $$R_3SiO(R_2SiO)_x(RSiO)_ySiR_3$$
$$|$$
$$QCOOH$$

wherein x has an average value of 0 or more, y has an average value of 1 or more and R and Q have the recited meanings.

12. A method according to claim 11 wherein Q contains from 2 to 5 carbon atoms and R and R′ each contains from 1 to 6 carbon atoms.

13. A method according to claim 12 wherein Q denotes $$|$$
$$-CH_2CHCH_3,$$

the —CH₂ portion thereof being bonded to a silicon atom.

14. A method according to claim 13 wherein each R denotes —CH₃.

* * * * *

UNITED STATES PATENT AND TRADEMARK OFFICE
CERTIFICATE OF CORRECTION

PATENT NO. : 4,604,478
DATED : August 5, 1986
INVENTOR(S) : Donnie R. Juen

It is certified that error appears in the above-identified patent and that said Letters Patent is hereby corrected as shown below:

In Col. 4, line 28, "

$$Cl(\underset{\underset{Ph}{|}}{\overset{\overset{Ph}{|}}{Si}}CH_2CH_2CH_2\overset{\overset{O}{\|}}{C}O)_n \underset{\underset{O\text{———}C=O}{|}}{\overset{\overset{Ph}{|}}{Si}}CH_2CH_2CH_2$$

"

should read $$-- \quad Cl(\underset{\underset{Cl}{|}}{\overset{\overset{Ph}{|}}{Si}}CH_2CH_2CH_2\overset{\overset{O}{\|}}{C}O)_n \underset{\underset{O\text{———}C=O}{|}}{\overset{\overset{Ph}{|}}{Si}}CH_2CH_2CH_2 \quad --.$$

Signed and Sealed this

Fourteenth Day of October, 1986

[SEAL]

*Attest:*

DONALD J. QUIGG

*Attesting Officer*   *Commissioner of Patents and Trademarks*